United States Patent
Zouta et al.

(10) Patent No.: US 9,670,315 B2
(45) Date of Patent: Jun. 6, 2017

(54) POLYCARBONATE RESIN COMPOSITION, AND FLUORESCENCE DETECTION/ANALYSIS SUBSTRATE PRODUCED USING POLYCARBONATE RESIN COMPOSITION

(71) Applicant: MITSUBISHI GAS CHEMICAL COMPANY, INC., Tokyo (JP)

(72) Inventors: Keiichi Zouta, Tokyo (JP); Atsuhiro Tokita, Tokyo (JP)

(73) Assignee: MITSUBISHI GAS CHEMICAL COMPANY, INC., Tokyo (JP)

(*) Notice: Subject to any disclaimer, the term of this patent is extended or adjusted under 35 U.S.C. 154(b) by 0 days.

(21) Appl. No.: 14/901,210

(22) PCT Filed: Jun. 19, 2014

(86) PCT No.: PCT/JP2014/066274
§ 371 (c)(1),
(2) Date: Dec. 28, 2015

(87) PCT Pub. No.: WO2015/001971
PCT Pub. Date: Jan. 8, 2015

(65) Prior Publication Data
US 2016/0152768 A1 Jun. 2, 2016

(30) Foreign Application Priority Data
Jun. 30, 2013 (JP) .................. 2013-137664

(51) Int. Cl.
| C08G 63/02 | (2006.01) |
| C08G 64/06 | (2006.01) |
| C08G 64/24 | (2006.01) |
| G01N 33/58 | (2006.01) |
| B29C 45/00 | (2006.01) |
| B29K 69/00 | (2006.01) |

(52) U.S. Cl.
CPC ............. C08G 64/06 (2013.01); C08G 64/24 (2013.01); G01N 33/582 (2013.01); G01N 33/585 (2013.01); B29C 45/0001 (2013.01); B29K 2069/00 (2013.01); B29K 2995/0018 (2013.01)

(58) Field of Classification Search
USPC ................................. 528/196, 198
See application file for complete search history.

(56) References Cited

U.S. PATENT DOCUMENTS

2008/0107858 A1* 5/2008 Meyer .................. C08G 64/406
428/64.1
2011/0269882 A1 11/2011 Kurokawa et al.

FOREIGN PATENT DOCUMENTS

| CN | 101536092 | 9/2009 |
| CN | 103044892 | 4/2013 |
| CN | 103481397 | 1/2014 |
| JP | 07-324138 | 12/1995 |
| JP | 2001-231556 | 8/2001 |
| JP | 2002-14100 | 1/2002 |
| JP | 2004-354131 | 12/2004 |
| JP | 2005-30913 | 2/2005 |
| JP | 2005-179410 | 7/2005 |
| JP | 2008-50382 | 3/2008 |
| JP | 4903518 | 1/2012 |

OTHER PUBLICATIONS

International Search Report issued in PCT/JP2014/066274, dated Sep. 9, 2014.
Zhao, Shuhui et al., "Preparation and Fluorescent Property of Eu(TTA)$_3$Phen Incorporated in Polycarbonate Resin"; Polymer Journal, vol. 38, No. 6; May 17, 2006; pp. 523-526.
Zhao et al., "Preparation and Fluorescent Property of Eu(TTA)$_3$Phen Incorporated in Polycarbonate Resin", Polymer Journal, vol. 38, No. 6, May 17, 2006, pp. 523-526.

* cited by examiner

Primary Examiner — Terressa Boykin
(74) Attorney, Agent, or Firm — Greenblum & Bernstein, P.L.C.

(57) ABSTRACT

An aromatic polycarbonate resin composition for a fluorescence detection and analysis substrate by which autofluorescence of an aromatic polycarbonate resin, which has been avoided as a resin for a fluorescence detection and analysis substrate due to a critical defect thereof of having fluorescence in a visible light wavelength region, is significantly decreased, and is highly heat-resistant and highly transparent; and a fluorescence detection and analysis substrate produced by melt molding performed on the aromatic polycarbonate resin composition. A polycarbonate resin composition, including a polycarbonate resin synthesized by an interfacial polymerization method, wherein the polycarbonate resin composition fulfills formula (1) below with respect to fluorescence emission of the composition when being excited by light having a wavelength of 290 nm, $$|\{F(310)-F(450)\}/\{F(400)-F(450)\}| \geq 40 \qquad \text{formula (1)}$$

where F(310), F(400) and F(410) are respectively fluorescence emission intensities at wavelengths of 310 nm, 400 nm and 450 nm.

15 Claims, 3 Drawing Sheets

EXCITATION LIGHT

45°

FLUORESCENCE
MEASUREMENT SIDE

45°

C LIGHT
SOURCE

LIGHT RECEIVING
SECTION

50mm

POLYCARBONATE RESIN COMPOSITION, AND FLUORESCENCE DETECTION/ANALYSIS SUBSTRATE PRODUCED USING POLYCARBONATE RESIN COMPOSITION

TECHNICAL FIELD

The present invention relates to a polycarbonate resin composition usable for a fluorescence detection and analysis substrate, and a fluorescence detection and analysis substrate formed using such a polycarbonate resin composition.

BACKGROUND ART

Conventionally, it is known that genetic analysis is possible by labeling a DNA as a target biomolecule with a fluorescent substance, directing laser light thereto to excite the fluorescent substance, and reading the generated fluorescence. The fluorescence of the fluorescent substance used for the labeling is very weak. Therefore, a material of a fluorescence detection and analysis substrate used for the genetic analysis as described above is often glass or silicon having low autofluorescence.

A material of a fluorescence detection and analysis substrate is required to be transparent, highly processable, highly chemical-resistant, highly heat-resistant, producible at low cost and the like in addition to being low in autofluorescence as described above. In the case where glass is used as a material of a fluorescence detection and analysis substrate, there are problems that, for example, the processability is not absolutely high and the production cost is high. In the case where silicon is used as a material of a fluorescence detection and analysis substrate, the processability is high because etching and photolithography are usable but there is a problem that the transparency is low.

In general, a plastic material used for a substrate (support) for fluorescence detection and analysis is preferably transparent from the point of view of detection sensitivity. Plastic materials that are being studied as a material of the substrate include, for example, an aromatic polycarbonate resin, a polystyrene resin, a saturated cyclic olefin-based resin, an acrylic resin and the like. With the above-described fluorescence detection and analysis method, in the case where the fluorescence (autofluorescence) derived from the substrate is high, the background of the substrate is high at the time of detection, and thus the S/N ratio is lowered to decrease the detection precision. Therefore, it is important that the material of a fluorescence detection and analysis substrate should be low in autofluorescence.

An aromatic polycarbonate resin has superb properties of transparency, heat resistance, transferability and the like, and thus is used in various fields for compact discs, light guide plates of liquid crystal devices, light diffusers and the like. Therefore, it has been attempted to use an aromatic polycarbonate resin for a fluorescence detection and analysis substrate (see, for example, Patent Document 1).

In the meantime, an aromatic polycarbonate resin has an aromatic ring, and therefore, has a characteristic of having higher potential autofluorescence than other transparent resins. Namely, although a material for a fluorescence detection and analysis substrate is generally required to have low autofluorescence (low background) in a visible light wavelength range (400 nm to 750 nm), the aromatic polycarbonate resin has autofluorescence in this visible light wavelength range and thus has high background. For this reason, the aromatic polycarbonate resin has a problem of not being suitable for a fluorescence detection and analysis substrate.

In such a situation, use of resins other than the aromatic polycarbonate resin, which is difficult to use for a fluorescence detection and analysis substrate, has been studied. Specifically, for example, as a fluorescence detection and analysis substrate that is transparent and has relatively low autofluorescence, a substrate formed of a saturated cyclic olefin-based resin has been proposed (see, for example, Patent Document 2).

A fluorescence detection and analysis substrate formed of a polyester containing alicyclic dicarboxylic acid and alicyclic diol as main components has also been proposed (see, for example, Patent Document 3). Patent Document 4 will be described later.

Patent Document 1: Japanese Laid-Open Patent Publication No. 2002-14100
Patent Document 2: Japanese Laid-Open Patent Publication No. 2001-231556
Patent Document 3: Japanese Laid-Open Patent Publication No. 2005-179410
Patent Document 4: Japanese Patent No. 4903518

SUMMARY OF INVENTION

Problem to be Solved by the Invention

Usually, a biochip may be treated at a high temperature while being handled, and a resin used for a substrate of the biochip is required to be heat-resistant. For example, a PCR (polymerase chain reaction) treatment on a fluorescence detection and analysis substrate is performed at 95° C. An autoclave sterilization is performed at a temperature as high as about 120° C.

Therefore, the saturated cyclic olefin-based resin, and the polyester resin containing the alicyclic dicarboxylic acid and alicyclic diol as main components, have a problem of not being satisfactorily heat-resistant.

In order to use aromatic polycarbonate, which is highly heat-resistant and highly transparent, for a fluorescence detection and analysis substrate, it has been attempted to decrease the autofluorescence of the aromatic polycarbonate with an additive or the like and an analysis substrate formed of such aromatic polycarbonate has been developed. Such an analysis substrate is described in, for example, Patent Document 4. An ultraviolet absorber or a phenol-based stabilizer is incorporated into the aromatic polycarbonate resin to decrease the fluorescence intensity. However, with this method, the substrate is excited by light that failed to be absorbed by the ultraviolet absorber or the like, and emits light. Thus, the substrate does not provide sufficient performance as a fluorescence detection and analysis substrate.

As described above, the aromatic polycarbonate has a problem of having high potential autofluorescence although having characteristics of being, for example, highly transparent, highly heat-resistant and highly transferable. No effective method for decreasing the autofluorescence has been found. In this situation, development of a material that is, for example, highly transparent, highly heat-resistant and highly transferable, has low autofluorescence and thus is suitable for a fluorescence detection and analysis substrate has been desired.

The present invention, made in light of the above-described situation, has an object of providing an aromatic polycarbonate resin composition for a fluorescence detection and analysis substrate that has significantly decreased autofluorescence and is highly heat-resistant and highly transparent, and a fluorescence detection and analysis substrate produced by melt molding performed on such an aromatic polycarbonate resin composition.

Means to Solve the Problem

Under the above-described situation, the present inventors actively studied autofluorescence of an aromatic polycarbonate resin; more specifically, specified from which autofluorescence is derived, and studied the mechanism of generation and increase of autofluorescence. As a result, the present inventors have found that autofluorescence of the aromatic polycarbonate resin is caused by various branch structures generated by heat provided during molding or the like. The present inventors have also found that the amount of the branch structures (amount of autofluorescence) is greatly influenced by the additive used or the type of the aromatic polycarbonate resin.

The present inventors have found the following: the contents of the compounds described later in detail are suppressed low by removing micrograins from flakes of a polycarbonate resin obtained by an interfacial polymerization method; and as a result, the amount of the branch structures in selected grains of the polycarbonate resin is decreased. The present inventors have also found the following: a transparent molded product obtained by, for example, injection molding performed on such selected grains has high autofluorescence that is characteristic of the polycarbonate resin at, or in the vicinity of, a fluorescence wavelength of 310 nm; however, the wavelength range of the autofluorescence is very narrow, and the autofluorescence is significantly low in a visible light region of 400 nm to 700 nm.

Namely, the present invention is as follows.

(I) A polycarbonate resin composition, comprising:
a polycarbonate resin synthesized by an interfacial polymerization method, wherein the polycarbonate resin composition fulfills formula (1) below with respect to fluorescence emission of the composition when being excited by light having a wavelength of 290 nm, $$\{F(310)-F(450)\}/\{F(400)-F(450)\}|\geq 40 \qquad \text{formula (1)}$$

where F(310), F(400) and F(410) are respectively fluorescence emission intensities at wavelengths of 310 nm, 400 nm and 450 nm.

(II) A polycarbonate resin fluorescence detection and analysis substrate, comprising the polycarbonate resin composition according to (I) above.

(III) The polycarbonate resin fluorescence detection and analysis substrate according to (II) above, wherein a total content of a compound represented by formula (A) below and a compound represented by formula (B) below in a hydrolysate obtained as a result of alkaline hydrolysis performed on the fluorescence detection and analysis substrate is 5 ppm by weight or less.

[Chemical formula 1]

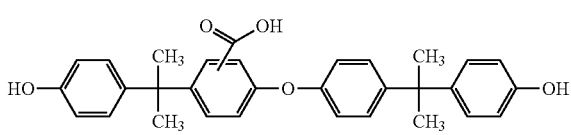

Formula (A)

-continued

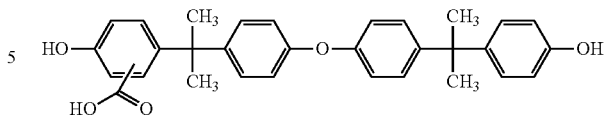

Formula (B)

(IV) The polycarbonate resin fluorescence detection and analysis substrate according to (III) above, wherein the total content of the compound represented by the formula (A) and the compound represented by the formula (B) in the hydrolysate obtained as a result of the alkaline hydrolysis performed on the fluorescence detection and analysis substrate is 3 ppm by weight or less.

(V) The polycarbonate resin fluorescence detection and analysis substrate according to any one of (II) through (IV) above, wherein the polycarbonate resin obtained by an interfacial polymerization method is in a form of flakes, and the polycarbonate resin fluorescence detection and analysis substrate is produced in a melt molding step performed on the flakes.

(VI) The polycarbonate resin fluorescence detection and analysis substrate according to (V) above, wherein the polycarbonate resin fluorescence detection and analysis substrate is produced using selected flakes containing grains having a grain diameter of 500 μm or longer at a content of 90% by weight or higher, the selected grains being obtained in a grain selection step of removing micrograins from the flakes.

(VII) The polycarbonate resin fluorescence detection and analysis substrate according to (VI) above, wherein the polycarbonate resin fluorescence detection and analysis substrate is produced using the selected grains obtained from the flakes in the grain selection step by use of wind power.

(VIII) The polycarbonate resin fluorescence detection and analysis substrate according to (VI) or (VII) above, wherein the polycarbonate resin fluorescence detection and analysis substrate is produced using the selected grains obtained by removing the micrograins caused to float by use of a ventilation unit.

(IX) The polycarbonate resin fluorescence detection and analysis substrate according to (VI) above, wherein the polycarbonate resin fluorescence detection and analysis substrate is produced using the selected grains obtained from the flakes in the grain selection step by use of a sieve.

(X) The polycarbonate resin fluorescence detection and analysis substrate according to (VII) or (VIII) above, wherein the polycarbonate resin fluorescence detection and analysis substrate is produced using the selected grains obtained from the flakes in the grain selection step by use of another sieve.

(XI) The polycarbonate resin fluorescence detection and analysis substrate according to (IX) or (X) above, wherein the polycarbonate resin fluorescence detection and analysis substrate is produced using the selected grains obtained by removing the micrograins in a state where the sieve is vibrated.

(XII) The polycarbonate resin fluorescence detection and analysis substrate according to any one of (IX) through (XI) above, wherein the polycarbonate resin fluorescence detection and analysis substrate is produced using the selected grains having a solution Y1 value of 1.30 or less.

(XIII) The polycarbonate resin fluorescence detection and analysis substrate according to any one of (V) through (XII) above, wherein the polycarbonate resin fluorescence detection and analysis substrate is produced using the flakes of the polycarbonate resin having a moisture content of 200 ppm or less as a result of being dried before being subjected to melt molding.

(XIV) The polycarbonate resin fluorescence detection and analysis substrate according to any one of (V) through (XIII) above, wherein the polycarbonate resin fluorescence detection and analysis substrate is produced by melt-molding the selected grains in the melt molding step in an atmosphere caused to have an oxygen concentration of 10000 ppm or less by addition of inert gas and/or pressure reduction.

(XV) The polycarbonate resin fluorescence detection and analysis substrate according to any one of (V) through (XIV) above, wherein the melt molding step is an injection molding step.

Effects of the Invention

An aromatic polycarbonate resin has conventionally been avoided from being used as a resin for a fluorescence detection and analysis substrate due to a critical defect thereof of having fluorescence in a visible light wavelength region. The present invention significantly decreases autofluorescence of the aromatic polycarbonate resin. Therefore, the present invention provides an aromatic polycarbonate resin composition, for a fluorescence detection and analysis substrate, which has little autofluorescence, has low background, and is highly heat-resistant and highly transparent, and also provides a fluorescence detection and analysis substrate formed using such an aromatic polycarbonate resin composition.

The aromatic polycarbonate resin composition for a fluorescence detection and analysis substrate, and the fluorescence detection and analysis substrate, according to the present invention are widely usable in the fields of biochemistry, medical diagnosis, drug discovery, microorganism investigation, food, environment, health care and the like; more specifically, are applicable for biochips such as a fluorescence detection and analysis substrate (DNA microarray), a protein chip (protein array), an enzyme chip, an antigen chip, an antibody chip, a cell chip, a microorganism chip and the like; a reaction chip using a lab-on-a-chip, an MEMS (MicroElectro Mechanical Systems) or the like, which includes a flow path, a reaction field, a detection unit and the like integrated in a compact manner by use of a precision processing technology using nanotechnology; and the like.

MODES FOR CARRYING OUT THE INVENTION

According to the present invention, selected grains are obtained by removing micrograins from flakes of a polycarbonate resin obtained by an interfacial polymerization method (grain selection step), and injection molding is performed on the selected grains to produce an injection-molded product (injection molding step). A molded product, for example, the injection-molded product, obtained as a result of such steps or the like has very low autofluorescence at a wavelength in a visible light region. A hydrolysate obtained as a result of alkaline hydrolysis performed on the injection-molded product of the polycarbonate resin produced according to the present invention contains compounds represented by the above-shown compounds (A) and (B) at a total content of 5 ppm by weight or less.

DESCRIPTION OF EMBODIMENTS

1. Polycarbonate Resin Flakes

Figure 1:
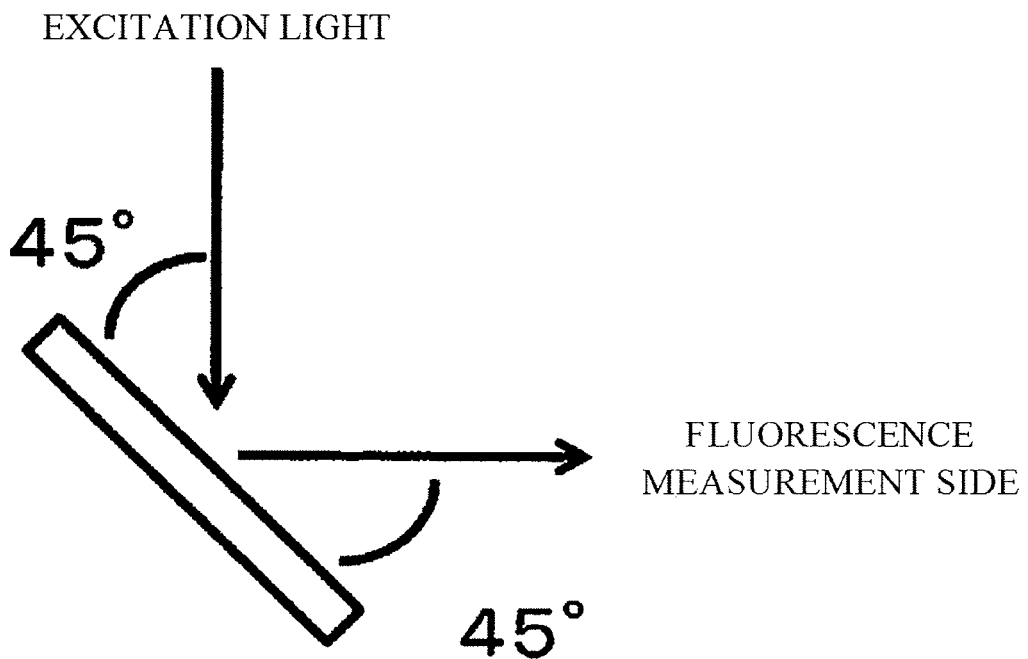
FIG. 1 schematically shows fluorescence spectrum measurement.

According to the present invention, flakes of a polycarbonate resin are produced by an interfacial polymerization method.

Specifically, a polycarbonate resin is obtained by reacting an aromatic dihydroxy compound or a combination of the aromatic dihydroxy compound and a small amount of polyhydroxy compound, with a carbonyl-based compound such as carbonyl chloride generally known as phosgene, carbonic diester represented by dimethyl carbonate or diphenyl carbonate, carbon monoxide, carbon dioxide or the like. The polycarbonate resin used in the present invention is a polymer or a copolymer of thermoplastic aromatic polycarbonate that may be straight-chained or branched to a degree at which the effect of the present invention is not lost.

Examples of the aromatic dihydroxy compound used as a material used to form the polycarbonate resin include 2,2-bis(4-hydroxyphenyl)propane [=bisphenol A], 2,2-bis(4-hydroxy-3,5-dimethylphenyl)propane, 2,2-bis(4-hydroxy-3,5-diethylphenyl)propane, 2,2-bis(4-hydroxy-(3,5-diphenyl)phenyl)propane, 2,2-bis(4-hydroxy-3,5-dibromophenyl)propane, 2,2-bis(4-hydroxyphenyl)pentane, 2,4'-dihydroxydiphenylmethane, bis-(4-hydroxyphenyl)methane, bis-(4-hydroxy-5-nitrophenyl)methane, 1,1-bis(4-hydroxyphenyl)ethane, 3,3-bis(4-hydroxyphenyl)pentane, 1,1-bis(4-hydroxyphenyl)cyclohexane, bis(4-hydroxyphenyl)sulfone, 2,4'-dihydroxydiphenylsulfone, bis(4-hydroxyphenyl)sulfide, 4,4'-dihydroxydiphenylether, 4,4'-dihydroxy-3,3'-dichlorodiphenylether, 4,4'-dihydroxy-2,5-diethoxydiphenylether, 1-phenyl-1,1-bis(4-hydroxyphenyl) ethane, 1,1-bis(4-hydroxy-3-methylphenyl)cyclohexane, 1-phenyl-1,1-bis(4-hydroxy-3-methylphenyl)ethane, and the like. Bis(4-hydroxyphenyl)alkanes are preferable. 2,2-bis(4-hydroxyphenyl)propane [called bisphenol A] is especially preferable. Such aromatic dihydroxy compounds may be used independently or as a mixture of two or more thereof.

The reaction by an interfacial polymerization method is caused as follows. The pH is generally kept at 10 or higher in the presence of an organic solvent inactive to the reaction or an alkaline aqueous solution, and an aromatic dihydroxy compound and a molecular weight adjusting agent (chain terminator) and, optionally, for example, an antioxidant that prevents oxidation of the aromatic dihydroxy compound are used. After the aromatic dihydroxy compound or the like is reacted with phosgene, a polymerization catalyst such as tertiary amine, quaternary ammonium or the like is added, and interfacial polymerization is performed. As a result, the polycarbonate resin is produced. The timing to add the molecular weight adjusting agent is not specifically limited and may be any time after the reaction with phosgene is performed before the start of the polymerization. The reaction temperature is, for example, 0 to 35° C., and the reaction time is, for example, several minutes to several hours.

Examples of the organic solvent inactive to the reaction include chlorinated hydrocarbons such as dichloromethane, 1,2-dichloroethane, chloroform, monochlorobenzene, dichlorobenzene, and the like; aromatic hydrocarbons such as benzene, toluene, xylene, and the like; etc. The molecular weight adjusting agent or the chain-terminator may be a compound having a monovalent phenol-based hydroxy group. Specific examples of such a compound include m-methylphenol, p-methylphenol, m-propylphenol, p-propylphenol, p-tert-butylphenol, p-long chain alkyl-substituted phenol, and the like. Examples of the polymerization catalyst include tertiary amines such as trimethylamine, triethylamine, tributylamine, tripropylamine, trihexylamine, pyridine, and the like; quaternary ammoniums such as trimethylbenzylammoniumchloride, tetramethylammoniumchloride, triethylbenzylammoniumchloride, and the like; etc.

The flakes of the polycarbonate resin are generated by, for example, as follows. A dichloromethane solution containing the polycarbonate resin produced by the interfacial polymerization method is dripped into warm water kept at about 45° C., and the solvent is removed by vaporization. Thus, the flakes of the polycarbonate resin are generated. Alternatively, a dichloromethane solution containing the polycarbonate resin produced by the interfacial polymerization method is put into methanol, and the deposited polymer is filtrated and dried. Thus, the flakes of the polycarbonate resin are generated. Still alternatively, a dichloromethane solution containing the polycarbonate resin produced by the interfacial polymerization method is pulverized while being stirred by a kneader with the temperature being kept at about 40° C., and then the solvent is removed with hot water of 95° C. or higher. Thus, the flakes of the polycarbonate resin are generated.

The polycarbonate resin flakes thus generated have an average grain diameter of, for example, about 50 to 300 µm, about 300 to 500 µm, about 500 to 700 µm, or about 700 to 900 µm, and of, for example, 600 µm, 800 µm, or the like. The grain diameter distribution of the flakes is 50 to 1500 µm, 100 to 1500 µm, 200 to 1500 µm, 300 to 1500 µm, or the like.

2. Grain Selection Step

According to the present invention, in a grain selection step, from the polycarbonate resin flakes, micrograins, namely, grains having a shorter grain diameter than that of the other grains contained in the flakes are removed to obtain selected grains. The selected grains contain grains having a predetermined reference grain diameter or longer at a predetermined reference content or higher. For example, the selected grains contain grains having a diameter of 200 µm or longer at a content of 90% by weight or higher. The reference grain diameter and the reference content of the selected grains are appropriately selected in accordance with the grain diameter distribution, the hue or the like of the flakes used. For example, the reference grain diameter is 100 µm, 200 µm, 500 µm, 1000 µm or the like, and the reference content may be 80% by weight, 90% by weight, 95% by weight, 97% by weight or the like.

In the grain selection step according to the present invention, a sieve having a predetermined size of openings, a wind-powered selection device using a ventilation unit, or the like is usable. Alternatively, a sieve and a wind-powered selection device may be used in combination.
1) Sieve The flakes may be sieved by a sieve having a predetermined size of openings, so that the micrograins are removed. Such a sieve may be, for example, a JIS standard sieve (JIS Z 8801-1), which is a metal net or a resin net. Alternatively, a sieve not conformed to the JIS may be used. Still alternatively, a classification device including a sieve may be used. In this case, the sieve may be, for example, vibrated, so that micrograins are efficiently removed from the flakes.
2) Wind-Powered Selection Device A wind-powered selection device having a ventilation function may be used to remove the micrograins in a state where the flakes are caused to float by ventilation. The wind-powered selection device causes the flakes to float while, for example, generating a wind, directed upward, in a cylinder by a ventilator (ventilation unit) provided in a bottom part of the cylinder. In this step, the micrograins are caused to fly by the wind power to pass through the cylinder and reach a diffusion chamber coupled to the cylinder, whereas the grains which have a longer diameter than that of the micrograins and are heavier than the micrograins drop in the cylinder by the gravitational force even if floating temporarily. As a result, the micrograins and the grains having a longer diameter than that of the micrograins are separated from each other. Thus, the selected grains are obtained.

The wind-powered selection device is not limited to having such a structure. For example, the pressure in the system may be reduced by an air discharge device located in a top part of the wind-powered selection device, and the grains to be selected may be caused to drop while the micrograins are moved to the system having the reduced pressure. Alternatively, the flakes may be supplied to a ventilation path having a diffusion chamber, and the grains to be selected may be caused to drop in the vicinity of a flake supply opening while the micrograins are caused to float to be transferred to the diffusion chamber. Natural wind may be used partially.

In this specification, the grain diameter of the selected grains is determined based on the value of the nominal size of openings (mm) of JIS Z 8801-1. For example, a grain which does not pass a sieve having nominal size of openings of 200 µm is defined as a grain having a grain diameter of 200 µm or longer. In the case where, for example, a sieve not conformed to the JIS or a wind-powered selection device was used to provide the selected grains, the selected grains may be caused to pass a sieve conformed to the JIS so that the reference grain diameter or the reference content are grasped.

3. Selected Grains

According to the present invention, a compound represented by the following formula (A) (hereinafter, the compound will be referred to as "compound A") and a compound represented by the following formula (B) (hereinafter, the compound will be referred to as "compound B") are each contained in a hydrolysate, obtained by alkaline hydrolysis performed on the selected grains, at a content of 5 ppm or less, preferably 3 ppm by weight or less, more preferably 2 ppm by weight or less, and especially preferably 1 ppm by weight or less. It is preferable that the content of each of compound A and compound B in the alkaline hydrolysate of the selected grains is 5 ppm by weight or less, or that the total content of compound A and compound B is 5 ppm by weight or less. The above-mentioned content of each of compound A and compound B and the total content of compound A and compound B are also preferably 3 ppm by weight or less, more preferably 2 ppm by weight or less, and especially preferably 1 ppm by weight or less. According to the present invention, the micrograins are removed from the polycarbonate resin flakes, so that the content of compound A and compound B in the flakes (selected grains) is suppressed low. As a result, a substrate that is more transparent is produced. The content (concentration) of each of compound A and compound B in the hydrolysate obtained by alkaline hydrolysis performed on the flakes (selected grains) is measured by the following method.

[Chemical formula 2]

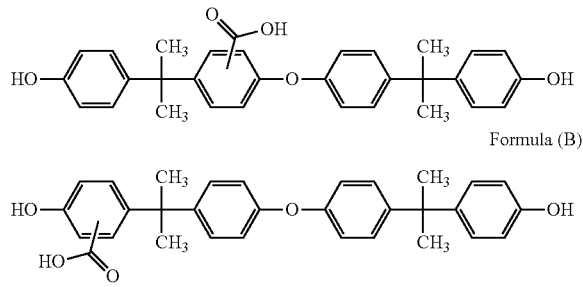

Formula (A)

Formula (B)

The content (concentration) of each of compound A and compound B in the hydrolysate obtained by alkaline hydrolysis performed on the flakes (selected grains) is measured by use of LC-MS/MS as follows. First, 0.1 g of sample of the flakes is dissolved in 10 ml of dichloromethane. To the resultant dichloromethane solution, 1.8 ml of 28% methanol solution of sodium methoxide, 8 ml of methanol and 2.6 ml of water are added, and stirred for 1 hour. To the resultant solution, 12 ml of 1 N aqueous solution of hydrochloric acid is added and stirred for 10 minutes. The system is acidified and then kept still. Then, an organic layer of dichloromethane separated from the water layer is put to a constant-volume vessel of 10 ml, and 2 ml of dichloromethane solution is sampled. The dichloromethane solution is dried and solidified in a nitrogen gas stream, and the resultant sample is dissolved in 2 ml of acetonitrile solution of 10 mg/l methoxysalicylic acid as an internal standard solution. The resultant solution is set as an LC-MS/MS measurement sample. This measurement sample is subjected to an LC-MS/MS measurement to calculate the content of each of compound A and compound B in the alkaline hydrolysate of the flakes (selected grains).

The content of each of compound A and compound B in the alkaline hydrolysate of the polycarbonate resin flakes is closely related with the hue of the flakes. Namely, flakes having a low content of compound A and compound B have a good hue close to being colorless, whereas flakes having a high content of compound A or compound B are colored yellow or amber and tends to have an inferior hue. According to the present invention, the selected grains obtained by removing micrograins from the flakes as described above are used, so that a pellet having a good hue is produced. The content of each of compound A and compound B in the alkaline hydrolysate of the selected grains is suppressed to 5 ppm by weight or less.

According to the present invention, the selected grains have a solution YI value of, preferably 1.30 or less, more preferably 1.20 or less, and especially preferably 1.00 or less in order to produce a molded product having a good hue closer to being colorless.

4. Melt Molding Step (Injection Molding Step)

According to the present invention, the above-described selected grains are produced by molding in a melt molding step such as, for example, an injection molding step. In the injection molding step, the selected grains are subjected to injection molding to produce an injection-molded product of the polycarbonate resin.

4-1. Components of the Melt-Molded (Injection-Molded) Product

In the melt molding step such as, for example, the injection molding step, the following components may be added in addition to the selected grains of the polycarbonate resin. The components that may be added include, for example, additives such as an antioxidant; a phosphorus-based or sulfur-based heat stabilizer; a benzotriazole-based or triazine-based ultraviolet absorber; a releasing agent such as carboxylic acid ester, polysiloxane compound, paraffin wax (polyolefin-based), polycaprolactone or the like; a photostabilizer; and the like.

Substances usable as the antioxidant include an organic sulfur compound, and an organic phosphorus compound such as phosphite or the like.

Usable as the heat stabilizer may be at least one selected from the group consisting of (a) phosphorous acid ester compound in which at least one ester in the molecules is esterified with phenol and/or phenol containing at least one alkyl group having a carbon number of 1 to 25, (b) phosphorous acid, and (c) tetrakis(2,4-di-tert-butylphenyl)-4,4'-biphenylene-di-phosphonite. Specific examples of the (a) phosphorous acid ester compound include trioctylphosphite, tridecylphosphite, triphenylphosphite, trisnonylphosphite, tris(octylphenyl)phosphite, tris(2,4-di-tert-butylphenyl) phosphite, tridecylphosphite, didecylmonophenylphosphite, dioctylmonophenylphosphite, diisopropylmonophenylphosphite, monobutyldiphenylphosphite, monodecyldiphenylphosphite, monooctyldiphenylphosphite, distearylpentaerythritoldiphosphite, diphenylpentaerythritoldiphosphite, bis(2,6-di-tert-butyl-4-methylphenyl)pentaerythritoldiphosphite, 2,2-methylenebis(4,6-di-tert-butylphenyl)octylphosphite, bis(nonylphenyl)pentaerythritoldiphosphite, bis(2,4-di-tert-butylphenyl)pentaerythritoldiphosphite, bis(2,6-di-tert-butyl-4-ethylphenyl)pentaerythritoldiphosphite, and the like. These substances may be used independently or as a mixture of two or more thereof.

Usable as the releasing agent may be at least one compound selected from the group consisting of aliphatic carboxylic acid, ester of aliphatic carboxylic acid and alcohol, aliphatic hydrocarbon compound having a number average molecular weight of 200 to 15000, and polysiloxane-based silicone oil. The aliphatic carboxylic acid may be saturated or unsaturated aliphatic monovalent, divalent or trivalent carboxylic acid. The "aliphatic carboxylic acid" encompasses alicyclic carboxylic acid. Preferable among such aliphatic carboxylic acids is monovalent or divalent carboxylic acid having a carbon number of 6 to 36. Especially preferable is aliphatic saturated monovalent carboxylic acid having a carbon number of 6 through 36. Specific examples of the aliphatic carboxylic acid include palmitic acid, stearic acid, caproic acid, capric acid, lauric acid, arachidic acid, behenic acid, lignoceric acid, cerotic acid, melissic acid, tetrariacontanoic acid, montanic acid, adipic acid, azelaic acid, and the like. As the aliphatic carboxylic acid in the ester of aliphatic carboxylic acid and alcohol, any of the substances listed above as the specific examples of the aliphatic carboxylic acid is usable. Usable as the alcohol may be saturated or unsaturated monovalent or polyvalent alcohol. Such alcohols may contain a substituent such as fluorine atom, aryl group or the like. Preferable among these alcohols is monovalent or polyvalent saturated alcohol having a carbon number of 30 or less. More preferable is aliphatic saturated monovalent or polyvalent alcohol having a carbon number of 30 or less. The "aliphatic compound" encompasses alicyclic compound. Specific examples of the alcohol include octanol, decanol, dodecanol, stearyl alcohol, behenyl alcohol, ethyleneglycol, diethyleneglycol, polypropyleneglycol, gricerin, pentaerythritol, 2,2-dihydroxyperfluoropropanol, neopentyleneglycol, ditrimethylolpropane, dipentaerythritol, and the like. The above-described ester compound may contain aliphatic carboxylic acid and/or alcohol as impurities, or may be a mixture of a plurality of compounds. Specific examples of the ester of aliphatic carboxylic and alcohol include beeswax (mixture containing myricyl palmitate as a main component), stearyl stearate, behenyl behenate, stearyl behenate, glycerinmonopalmitate, glycerinmonostearate, glycerindistearate, glycerintristearate, pentaerythritolmonopalmitate, pentaerythritolmonostearate, pentaerythritoldistearate, pentaerythritoltristearate, pentaerythritoltetrastearate, and the like. Examples of the aliphatic hydrocarbon having a number average molecular weight of 200 to 15000 include liquid paraffin, paraffin wax, microwax, polyethylene wax, Fischer-Tropsch wax, α-olefin oligomer having a carbon number of 3 to 12, and the like. The "aliphatic hydrocarbon" encompasses alicyclic hydrocarbon. Such a hydrocarbon compound may be partially oxidized. Among the above-listed substances, paraffin wax, polyethylene wax, and partially oxidized polyethylene wax are preferable. Paraffin wax and polyethylene wax are more preferable. The number average molecular weight is preferably 200 to 5000. Such an aliphatic hydrocarbon may be formed of a single substance or a mixture of substances having any of various components or any of molecular weights, as long as the main component is contained at a content in the above-described range. Examples of the polysiloxane-based silicone oil include dimethyl silicone oil, phenylmethyl silicone oil, diphenyl silicone oil, fluoridated alkyl silicone oil, and the like. Two or more of these may be combined.

Necessary amounts of such additives may be entirely mixed together directly by a tumbler, a mixer or the like and added to the selected grains of the polycarbonate resin. Alternatively, a master batch formed of all the additives may be formed and used to produce a melt-molded product such as an injection-molded product or the like. Still alternatively, necessary amounts of a part of the additives are entirely mixed together, and a master batch of the other additives may be formed.

It is preferable that the selected grains are dried to decrease the water content thereof before being used for melt molding such as injection molding or the like. Specifically, the selected grains are dried to suppress the water content thereof to preferably 300 ppm by weight or less, and more preferably 200 ppm by weight or less. The suppression of the water content of the selected grains prevents molding faults which may otherwise occur to the selected grains, for example, foaming at the time of injection molding.

4-2. Melt Molding Steps Other than the Injection Molding Step

The melt molding method used to produce the substrate, which will be described in detail later is not limited to any specific method, and may be any conventionally known resin molding method. Specific examples of the melt molding method include commonly used molding methods such as injection molding, injection compression molding, compression molding, extrusion molding, hot emboss (nanoimprint) molding, and the like. Injection molding and injection compression molding are especially preferable from the point of view of productivity and freedom of shape. At the time of injection molding, a supercritical fluid may be introduced together with the resin into the cylinder. In this case, the fluidity of the resin is increased, and the transferability of microscopic shapes (grooves, holes or the like) is also increased.

In the melt molding step, the selected grains are subjected to melt molding in an atmosphere having an oxygen concentration in the system of 10000 ppm or less, preferably 5000 ppm or less, and more preferably 2000 ppm or less. Such an atmosphere is realized by addition of inert gas and/or pressure reduction.

5. Fluorescence Detection and Analysis Substrate

Now, a fluorescence detection and analysis substrate according to the present invention will be described. A "fluorescence detection and analysis substrate" is a generic term of members that are used for a device (analyzer, microscope) that detects fluorescence as a signal and are formed of a material having low autofluorescence. Especially in the fields of biochemistry, medical diagnosis (clinical examination), drug discovery, microorganism investigation, food, environment, health care and the like, the term "fluorescence detection and analysis substrate" refers to a device substrate usable to manipulate and analyze a biological substance or a chemical compound as a target of analysis at high precision and efficiency. Specifically, the "fluorescence detection and analysis substrate" may be, for example, a biochip, a reaction chip or the like.

The fluorescence detection and analysis substrate is not limited to having any specific shape, and may be substrate-like (glass slide-like, card-like, disc-like, etc.), fiber-like, spherical, tube-like, film-like, (micro)well-like, or the like. The fluorescence detection and analysis substrate may be a member directly subjected to detection light or a member located in the vicinity of a member directly subjected to detection light.

A "biochip" is a generic term of devices, with which a biological substance, a compound or the like as a target of analysis is immobilized to a substrate (support), such immobilized substances (probes) or such an immobilized substance (probe) and another compound (target) are put into contact with each other, and the resultant specific interaction is detected. The biochip is mainly used for functional analysis of a biomolecule, integration of manipulations, sensing or the like. The "interaction" encompasses an interaction by which a chemical structure formed by ion bond or covalent bond is changed by a chemical reaction, and also encompasses an action which may produce a situation where a chemical structure is bonded with another substance in another mode such as hydrogen bond, coordinate bond, Van der Waals force, chemical adsorption, physical adsorption or the like.

Specific examples of the above-described biological substance include DNA fragment, synthesized nucleotide, protein, enzyme, antigen, antibody, epitope, sugar chain, glycoprotein, glycolipid, cell and the like. The "fluorescence detection and analysis substrate" according to the present invention encompasses biochips such as a fluorescence detection and analysis substrate usable for extraction, purification, proliferation, recovery, analysis or the like of DNA (DNA microarray), a protein chip usable for purification, crystallization, expression, analysis, condition search or the like of protein (protein array), an antibody chip, a sugar chain chip usable to analyze sugar chain capturing or the sugar chain-protein interaction, a cell chip usable for cell separation and analysis, and the like.

The fluorescence detection and analysis substrate according to the present invention may be surface-modified or surface-treated to such a degree at which the effect of the present invention is not spoiled. The surface modification may be performed by any of various methods. Specifically, for example, introduction of an aldehyde group is preferable, by which physiologically active substances are covalent-bonded to each other on the substrate to increase the strength of immobilization.

According to a preferable method for introducing an aldehyde group, an amino group is introduced and then multifunctional aldehyde is reacted therewith. Methods for introducing an amino group include treatment with an amino group-containing silane coupling agent, plasma treatment in a nitrogen atmosphere, coating with an amino group-containing polymeric substance, and the like. Treatment with an amino group-containing silane coupling agent is preferable form the point of view of simplicity and uniformity of the treatment.

A preferable example of the multifunctional aldehyde is glutaraldehyde. The surface treatment may be performed by any of various methods. The treatment may be performed with, for example, cationic polymer, poly-L-lysine, polyethyleneglycol (derivative), phosphatidylcholine group-containing polymer or the like.

EXAMPLES

Hereinafter, the present invention will be further described by way of examples. The present invention is not limited to any of the following examples and may be altered without departing from the gist of the invention.

In these examples, first, from flakes (grain diameter distribution: 50 to 1200 µm; average grain diameter: 800 µm; solution YI value: 1.33) of a polycarbonate resin to be commonly used among the examples (H-4000F produced by Mitsubishi Engineering-Plastics Corporation; aromatic polycarbonate resin), micrograins were removed. Samples of the resultant selected grains are shown in Table 1 below. The samples were each injection-molded to produce a molded product. Regarding the molded products, the fluorescence spectrum and the total concentration of compounds A and B were measured.

TABLE 1

|  | Sample 1 | Sample 2 | Comparative Sample 1 |
| --- | --- | --- | --- |
| Selection method | Sieve of 500 µm openings | Classification device | Not selected |
| Micrograins removed | Grains of less than 500 µm are removed | Grains of less than 500 µm are removed | Not removed |
| Micrograins remaining | ND | 3-5% by weight | — |
| Solution YI value of the flakes | 1.10 | 1.12 | 1.33 |
| Total concentraion of compounds A and B in the flakes | ND | ND | 4.0 ppm by weight |

The selected flakes of sample 1 were obtained by removing the micrograins having a grain diameter less than 500 µm from the flakes of the above-described resin by use of a sieve having openings of a size of 500 µm. The selected flakes of sample 2 were obtained by removing the micrograins from the flakes of the above-described resin by use of a classification device (turbo screener produced by Freund-Turbo Corporation) capable of automatically selecting flakes.

The flakes of sample 2 were selected as follows by the classification device. First, a blade in a synthetic resin cylindrical net having openings of a size of 500 µm provided in the classification device was rotated at a high speed. In this state, air was absorbed by an absorption device (ventilation unit) to supply the flakes, together with the air, to the inside of the cylindrical net from an opening at an end of the cylindrical net, and thus small vibrations were caused to the net. As a result, most of the flakes having a small grain diameter dropped through a side surface of the cylindrical net relatively quickly. By contrast, selected grains which did not pass the net and a small amount of flakes having a small grain diameter moved to an end opposite to the end through which the flakes were supplied, and dropped through an opening at the opposite end.

The resultant selected flakes of sample 2 obtained by use of such a classification device contained a small amount of flakes having a small grain diameter. Namely, the selected grains of sample 1 did not contain micrograins having a grain diameter smaller than, or equal to, the size of the openings of the sieve used, whereas the selected grains of sample 2 contained grains having a grain diameter less than 500 µm at a content of about 3 to 5% by weight with respect to the total weight of the selected grains. In this manner, use of a classification device causes a small amount of flakes having a small grain diameter to be contained, but realizes quick selection of a larger amount of flakes by use of a centrifugal force. Comparative sample 1 was formed of the flakes of the resin with no selection being performed.

Next, an injection-molded product was produced by use of the selected grains of sample 1 described above. For producing the injection-molded product, an injection molding device 100 shown in FIG. 3 was used. The injection molding device 100 includes a molding cylinder 10 including a resin introduction part 11 at a tip thereof, a screw 15 built in the molding cylinder 10, a hopper 20 that is attached to the molding cylinder 10 and supplies selected grains 1 as a material of the injection-molded product to the molding cylinder 10, a screw driving device 18 attached to a rear end 16 of the screw 15, and the like. The screw 15 located in the molding cylinder 10 is an in-line screw that plasticizes and melts the selected grains 1 and also acts as a plunger. A heater (not shown) is attached to an outer circumference of the molding cylinder 10, so that the selected grains 1 present in a gap 17 between the molding cylinder 10 and the screw 15 are plasticized and melted. The selected grains 1 and additives (not shown) described later were transported in a gas stream into the hopper 20 from a resin storage part via a pipe (not shown) and a transportation part 21. The composition of the selected grains 1 and the additives used was as follows.

Selected grains 1 (sample 2 described above; polycarbonate resin lupilon H-4000F (produced by Mitsubishi Engineering-Plastics Corporation)): 99.92 parts by weight Adeka stab PEP36 (bis(2,6-di-tert-butyl-4-ethylphenyl) pentaerythritoldiphosphite; produced by Adeka Corporation)): 0.05 parts by weight Rikemal S100A (glycerinmonostearate; produced by Riken Vitamin Co., Ltd.): 0.03 parts by weight Downstream with respect to a discharge part 22 attached to the hopper 20, a blower (not shown) is located. The blower was actuated to make the pressure inside the hopper 20 negative, and the selected grains 1 in a flake state were transported in a gas stream into the hopper 20 from the storage part of the polycarbonate resin as the material of the injection-molded product via the pipe and the transportation part 21. It should be noted that the method of transportation of the selected grains 1 from the resin storage part to the hopper 20 may be any method.

Figure 3:
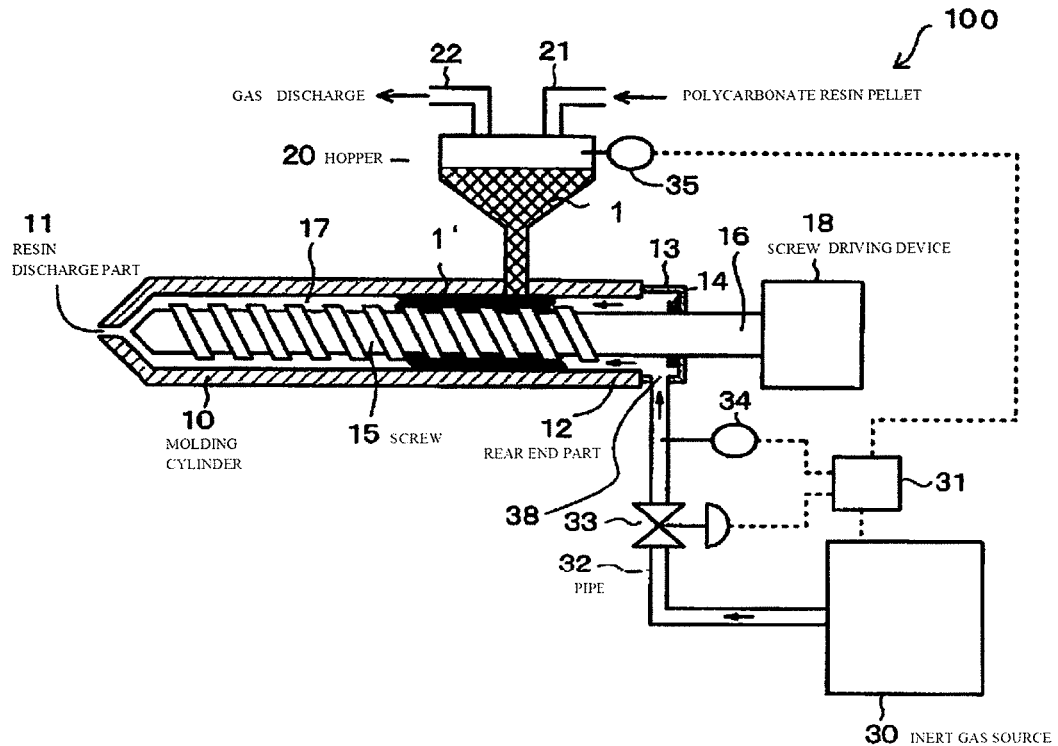
FIG. 3 shows an injection molding device usable to produce an injection molded-product.
Figure 4:
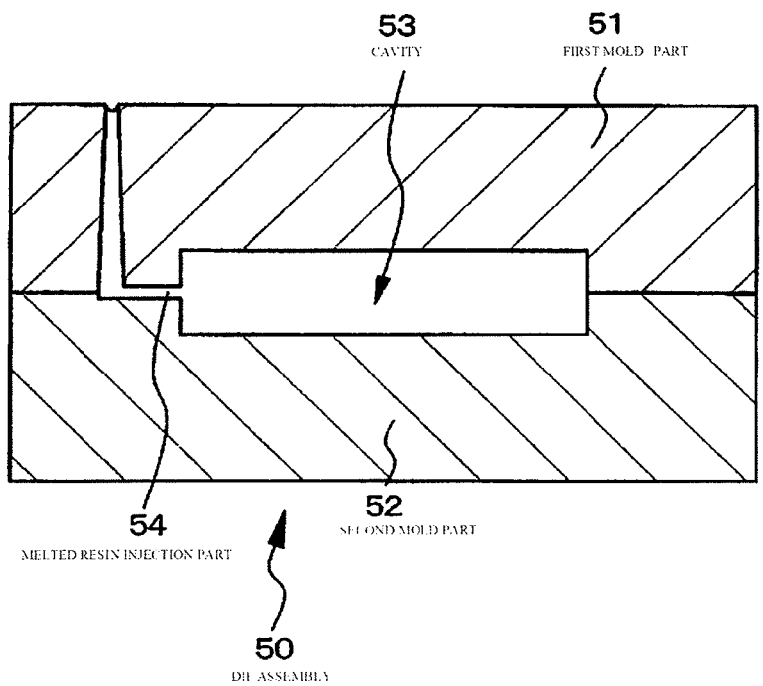
FIG. 4 schematically shows a mold usable for injection molding.

The selected grains 1 transported from the hopper 20 to the molding cylinder 10 were heated, plasticized, melted and transported by the molding cylinder 10 and the screw 15. The barrel (molding cylinder) 10 had been set to a melting temperature of 240° C. The screw driving device 18 was actuated to rotate the screw 15 while pushing the screw 15 forward to pressurize the melted selected grains 1' containing the additives in the molding cylinder 10, and thus the melted selected grains 1' were injected from the resin introduction part 11 toward a melted resin injection part 54 (see FIG. 4) of a mold assembly 50. In the mold assembly 50, the melted selected grains 1' were supplied via the melted resin injection part 54 into a cavity 53 provided between a first mold part 51 and a second mold part 52. The melted selected grains 1' were provided to fill a portion of the gap 17 between the molding cylinder 10 and the screw 15, the portion being between a position of the molding cylinder 10 to which the hopper 20 was attached and the resin introduction part 11. In FIG. 3, the melted selected grains 1' are shown to fill a part of the portion of the gap 17.

To a rear end part 12 of the molding cylinder 10 on the screw driving device 18 side, an airtight state forming member 13 is attached that puts the rear end part 12 into an airtight state. A sealing member 14 that puts a space between the airtight state forming member 13 and the screw 15 into an airtight state is attached to the airtight state forming member 13. Such a structure kept the space, in the molding cylinder 10 in which inert gas (e.g., nitrogen gas having a purity of about 99.99%) was flowing, in an airtight state. As a result, the oxygen concentration in the molding cylinder 10 was suppressed to about 100 ppm.

In the case where the molding cylinder 100 itself is airtight, neither the airtight state forming member nor the sealing member is necessary. FIG. 3 shows the flow of the inert gas with arrows.

The injection molding device 100 also includes an inert gas source 30 and a pipe 32 used to introduce inert gas from the inert gas source 30 into the molding cylinder 10. The pipe 32 is attached to a position of the molding cylinder 10 that is on the side of the screw driving device with respect to the position of the molding cylinder 10 to which the hopper 20 is attached; more specifically, the pipe 32 is attached to the airtight state forming member 13. The pipe 32 may be attached to the rear end part 12 of the molding cylinder 10 on the side of the screw driving device. In the middle of the pipe 32, a pressure control valve 33 and a pressure sensor 34 are provided. In order to detect the pressure in the hopper 20, the hopper 20 is provided with a second pressure sensor 35. The pressure control valve 33 and the pressure sensors 34 and 35 may be of a known system and structure. Outputs of the pressure sensors 34 and 35 are sent to a pressure control device 31, and an output of the pressure control device 31 controls the actuation of the pressure control valve 33 and the inert gas source 30.

An inert gas injection opening 38 is a gap through which the inert gas is allowed to pass but into which the polycarbonate resin as the material of the injection-molded product is not allowed to flow. There is no specific limitation on the position or the shape of the inert gas injection opening 38 as long as the inert gas passes is allowed to pass through, and the polycarbonate resin as the material of the injection-molded product is prevented from flowing into, the inert gas injection opening 38. The inert gas injection opening 38 may be linear, and more preferably circular, instead of being dot-like.

The inert gas was caused to flow from the inert gas source 30 to the outside of the system via the pipe 32, the inert gas injection opening 38, the molding cylinder 10 and the discharge part 22 attached to the hopper 20. At this point, the hopper 20 was filled with the selected grains 1, and the selected grains 1 were plasticized in the portion of the gap 17 between the molding cylinder 10 and the screw 15, the portion being between the position of the molding cylinder 10 to which the hopper 20 was attached and the resin introduction part 11.

In this state, the pressure in the part of the molding cylinder in which the inert gas flows (specifically, the rear end part 12) is, for example, higher than the atmospheric pressure by about $2 \times 10^3$ Pa (0.02 kgf/cm$^2$). The pressure of the inert gas or the change of the pressure in the rear end part 12 may be detected by the pressure sensor 34. Based on the detection result of the pressure, the pressure control valve 33 may be controlled via the pressure control device 31 to control the flow rate of the inert gas. At the time when the selected grains 1' were transported in a gas stream into the hopper 20, the pressure inside the hopper 20 was made negative. As a result, the pressure of the inert gas flowing from the inert gas source 30 to the outside of the system via the pipe 32, the molding cylinder 10 and the hopper 20 was changed. Such a change of the pressure inside the hopper 20 was detected by the second pressure sensor 35, and the pressure of the inert gas in the rear end part 12 was detected by the pressure sensor 34. Based on the detection results of these pressures, it was possible to control the pressure control valve 33 and the inert gas source 30 via the pressure control device 31 to control the flow rate of the inert gas. Therefore, even though the pressure inside the hopper 20 was changed, the flow rate of the inert gas flowing from the inert gas source 30 to the outside of the system via the pipe 32, the inert gas injection opening 38, the molding cylinder 10 and the hopper 20 was kept substantially constant.

Gas that was generated from the selected grains 1' plasticized and melted in the gap 17 between the molding cylinder 10 and the screw 15 was discharged to the outside of the system from the discharge part 22 via the hopper 20, together with the inert gas flowing in the molding cylinder 10.

In example 1, the oxygen gas concentration in the hopper 20 and the molding cylinder 10 to which the selected grains 1 as the material of the injection-molded product were put was controlled to 200 ppm by nitrogen gas supplied from the inert gas source 30. The oxygen gas concentration may be decreased by use of an injection molding device 110, in which the molding cylinder 10 has a gas discharge opening (vent part) 19 as shown in FIG. 3. In the injection molding device 110, the pressure inside the system may be easily reduced by use of a vacuum pump (not shown) via the gas discharge opening (vent part) 19, or nitrogen may be easily injected while reducing the pressure inside the system.

The injection molding was performed under the following conditions. Injection molding device: Injection molding device TR100EH2 produced by Sodick Plustech Co., Ltd.

| | |
|---|---|
| Molded product size: | 100 mm long × 100 mm wide × 3 mm thick |
| Molding temperature: | 280° C. |
| Mold temperature: | 100° C. |
| Molding cycle | 40 seconds |

By such injection molding, the polycarbonate resin was injected from the resin introduction part 11 (see FIG. 3) to fill the cavity 53. The polycarbonate resin filling the cavity 53 was cooled to produce an injection-molded product having a shape corresponding to the cavity 53 (see FIG. 4).

The injection-molded products in examples 1 through 4 and comparative example 1 as shown in Table 2 below were produced by use of the selected grains of sample 1, sample 2 and comparative sample 1 described above. The injection molded-products in examples 2 through 4 and comparative example 1 were produced by the same method as in example 1 described above except for the oxygen gas concentration at the time of molding.

The fluorescence intensity of each of flat-plate test pieces obtained in examples 1 through 4 and comparative example 1 was measured.

The fluorescence intensity was evaluated as follows. Each of 3 mm-thick flat-plate test pieces obtained in examples 1 through 4 and comparative example 1 was set as shown in FIG. 1 such that the angle of incidence of a light beam of excitation light would be 45 degrees and the outgoing angle on the fluorescence measurement side would also be 45 degrees. The fluorescence emission spectrum was measured in a three-dimensional measurement mode and a fluorescence data mode by use of a fluorescence spectrophotometer F-4500 produced by Hitachi High-Technologies Corporation.

The measurement conditions were as follows: excitation-side sampling interval: 10 nm; excitation-side slit interval: 1 nm; fluorescence-side sampling interval: 5 nm; fluorescence-side slit interval: 2.5 nm; scan speed: 240 nm/min.; PMT voltage: 950 V; response: 0.004 seconds; spectrum correction: ON; shutter control: ON. The wavelength of the excitation light was 290 nm.

The fluorescence emission spectrum was measured at room temperature.

In various analyses performed by use of a fluorescence detection and analysis substrate, fluorescence emitted by each sample is detected. Therefore, lower autofluorescence intensity of the substrate is more preferable.

In general, the wavelength of the fluorescence emitted by an analysis sample is in the visible light region. Therefore, it is effective that autofluorescence of the fluorescence detection and analysis substrate is significantly low in this region. A polycarbonate fluorescence detection and analysis substrate uses polycarbonate as a material. Therefore, fluorescence emission derived from the structure of polycarbonate is observed at or in the vicinity of 310 nm. As a result of studies, the present inventors have found that fluorescence emission in the visible light region is caused by various branch structures generated by heat given in a step of molding or the like. It has also been found that the fluorescence intensity at or in the vicinity of 310 nm is decreased, and instead, the fluorescence intensity of a wavelength in the visible light region of about 330 to 410 nm, longer than 310 nm, is significantly increased.

Figure 5:
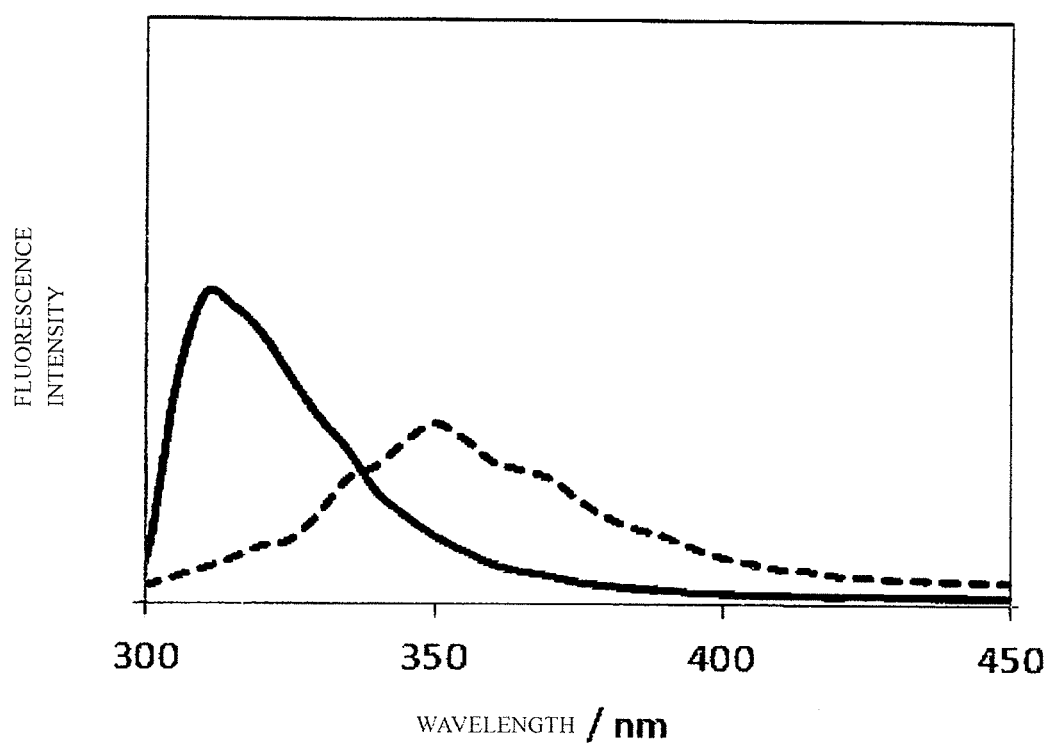
FIG. 5 shows fluorescence spectra of polycarbonate resin molded products.

As described above, the fluorescence emission of a sample to be analyzed by use of the fluorescence detection and analysis substrate is often in the visible light region. Therefore, it is preferable that emission from the analysis substrate is not present in the visible light region. According to the studies of the present inventors, low emission from the polycarbonate analysis substrate in the visible light region may be rephrased as the fluorescence intensity at 310 nm, which is the original fluorescence emission of polycarbonate, being higher than the fluorescence intensity in the visible light region, which is longer than 310 nm. FIG. 5 shows fluorescence spectra of the polycarbonate resin molded products. The solid line represents a preferable fluorescence spectrum from the fluorescence detection and analysis substrate. The fluorescence intensity of the fluorescence spectrum represented by the dashed line is too high in the visible light region, and thus a substrate having such a fluorescence spectrum is not usable.

Based on the above, the present inventors have found that an effective polycarbonate fluorescence detection and analysis substrate is a molded product fulfilling the following formula (1).

$$|\{F(310)-F(450)\}/\{F(400)-F(450)\}| \geq 40 \qquad \text{formula (1)}$$

In formula (1), F(310), F(400) and F(450) are respectively relative values of the fluorescence emission intensity at wavelengths of 310 nm, 400 nm and 450 nm.

TABLE 2

|  | Example 1 | Example 2 | Example 3 | Example 4 | Comparative Example 1 | Comparative Example 2 | Comparative Example 3 |
|---|---|---|---|---|---|---|---|
| Flakes used | Sample 1 | Sample 2 | Sample 2 | Sample 2 | Comparative Sample 1 | — | — |
| Micrograins removed | Less than 500 μm | Less than 500 μm | Less than 500 μm | Less than 500 μm | Not removed | — | — |
| Oxygen concentration at the time of molding | 200 ppm | 1000 ppm | 500 ppm | 200 ppm | 1000 ppm | — | — |
| Total concentration of compounds A and B | ND | ND | ND | ND | 11.5 ppm | — | — |
| Value of {F(310)-F(450)}/{F(400)-F(450)} | 95 | 89 | 70 | 103 | 5 | 27 | 15 |

As is clear from Table 2, in examples 1 through 4, the value of formula (1) is clearly larger than 40, which indicates that the fluorescence of the visible light wavelength region was decreased.

The value of the left side of formula (1) is preferably 45 or greater, more preferably 55 or greater, and still more preferably 65 or greater.

In comparative example 2 and comparative example 3, the formula (1) is of polycarbonate resin compositions respectively obtained by incorporating 0.1% and 0.3% of a benzotriazole-based ultraviolet absorber into aromatic polycarbonate having a structural viscosity index N of 1.2 or less described in Patent Document 4.

From the results shown in Table 2, it is seen that the polycarbonate resin compositions of comparative example 2 and comparative example 3 have a small value of formula (1). Therefore, the resin composition in each of comparative example 2 and comparative example 3 had a fluorescence intensity in the visible light region higher than that of the fluorescence intensity at 310 nm originally derived from the aromatic polycarbonate, and thus did not provide satisfactory performance of the fluorescence detection and analysis substrate.

The injection-molded products in examples 1 through 4 were subjected to alkaline hydrolysis, and LC-MS/MS measurement or the like was performed on the resultant hydrolysates to specify and quantify the impurities contained in examples 1 through 4. As a result, compound A represented by formula (A) was not detected in any of examples 1 through 4. By contrast, in comparative example 1, compound A was contained at a concentration of 11.5 ppm by weight. Based on this, it has been confirmed that the concentration of compound A is related to the value of the fluorescence intensity.

In order to check the relationship between the hue of the polycarbonate flakes as the material to be subjected to the injection molding and the fluorescence intensity of the injection-molded product, the solution YI values of sample 1, sample 2 and comparative sample 1 of the flakes, as the materials of the injection-molded products in examples 1 through 4 and comparative example 1, were measured.

Figure 2:
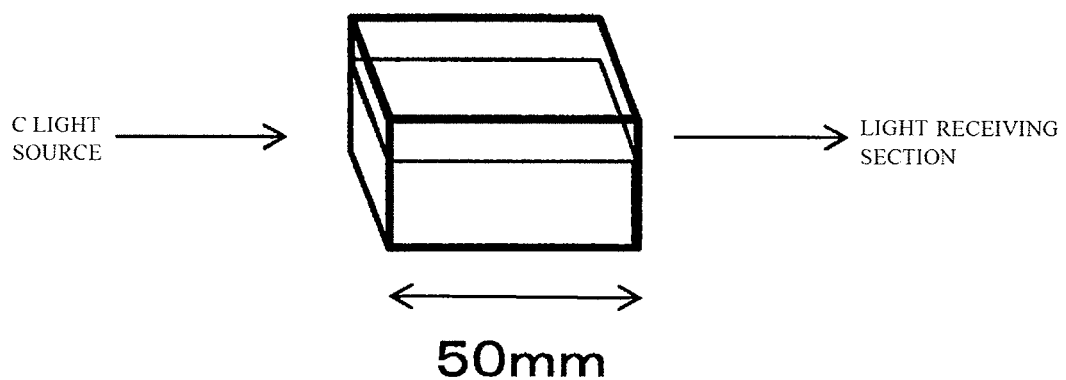
FIG. 2 schematically shows a method for measuring a solution YI value.

FIG. 2 schematically shows the measurement of a solution YI value. The solution YI value was measured as follows. Twelve grams of each flake sample was dissolved in 80 ml of dichloromethane (special grade) and put into a transparent glass cell having an optical path length of 50 mm. The solution YI value was measured by a spectrophotometer SD6000 produced by Nippon Denshoku Industries Co., Ltd.

The solution YI values of sample 1, sample 2 and comparative sample 1 of the polycarbonate flakes as the materials to be subjected to injection molding in examples 1 through 4 and comparative example 1 were compared. As is clear from Table 3 below, the solution YI value of each of sample 1 and sample 2 was smaller than the solution YI value of comparative sample 1. From these results, it is seen that in the case where the components having a small grain diameter were not removed from the flakes, the solution YI value was increased and the hue was deteriorated. The total concentration of compounds A and B in the flakes of each of samples 1 and 2 was very low, more specifically, lower than the detection limit (ND). By contrast, the total concentration of compounds A and B in the flakes of comparative sample 1 was 4.0 ppm by weight. Based on these results, it has been confirmed that the total concentration of compounds A and B is an element related to the hue of the molded product.

TABLE 3

|  | Sample 1 | Sample 2 | Comparative Sample 1 |
|---|---|---|---|
| Selection method | Sieve of 500 μm openings | Classification device | Not selected |
| Micrograins removed | Grains of less than 500 μm are removed | Grains of less than 500 μm are removed | Not removed |
| Micrograins remaining | ND | 3-5% by weight | ND |
| Solution YI value of the flakes | 1.10 | 1.12 | 1.33 |
| Total concentraion of compounds A and B in the flakes | ND | ND | 4.0 ppm by weight |

Specifically, neither compound A nor compound B was detected from the flake materials having a solution YI value of 1.30 or less.

[Chemical formula 3]

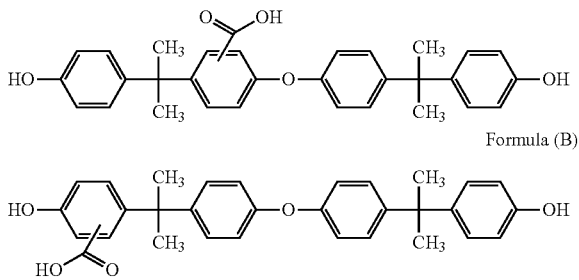

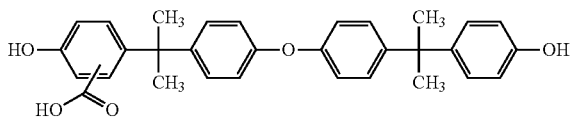

Based on the above results, it has been confirmed that an injection-molded product produced by removing a predetermined amount of components having a small grain diameter contained in the polycarbonate resin flakes has a significantly lower fluorescence intensity in the visible light region as well as improved hue and transparency, and provides greater effects than an injection-molded product produced by a conventional method of adding an additive to the flakes.

As described above, according to the present invention, an injection-molded product or the like is produced by removing micrograins and selecting grains from polycarbonate flakes obtained by an interfacial polymerization method, and thus a polycarbonate resin fluorescence detection and analysis substrate having very low autofluorescence is provided.

So far, the present invention has been described based on preferable examples. The present invention is not limited to any of these examples. The structure of the injection molding device, materials used, injection molding conditions and the like described in the examples are illustrative, and may be appropriately altered.

The invention claimed is:
1. A polycarbonate resin composition, comprising:
a polycarbonate resin synthesized by an interfacial polymerization method, wherein the polycarbonate resin composition fulfills formula (1) below with respect to fluorescence emission of the composition when being excited by light having a wavelength of 290 nm,

|{F(310)−F(450)}/{F(400)−F(450)}|40    formula (1)

where F(310), F(400) and F(410) are respectively fluorescence emission intensities at wavelengths of 310 nm, 400 nm and 450 nm, and
wherein the polycarbonate resin comprises selected grains having a solution YI value of 1.30 or less.
2. A polycarbonate resin fluorescence detection and analysis substrate, comprising the polycarbonate resin composition according to claim 1.
3. The polycarbonate resin fluorescence detection and analysis substrate according to claim 2, wherein a total content of a compound represented by formula (A) below and a compound represented by formula (B) below in a hydrolysate obtained as a result of alkaline hydrolysis performed on the fluorescence detection and analysis substrate is 5 ppm by weight or less

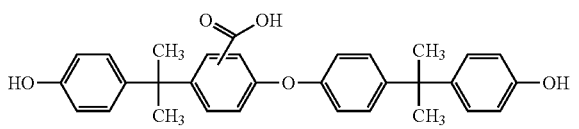

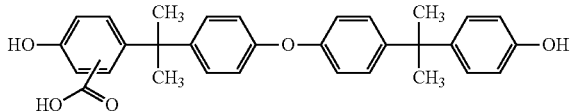

Formula (B)

4. The polycarbonate resin fluorescence detection and analysis substrate according to claim 3, wherein the total content of the compound represented by the formula (A) and the compound represented by the formula (B) in the hydrolysate obtained as a result of the alkaline hydrolysis performed on the fluorescence detection and analysis substrate is 3 ppm by weight or less.

5. The polycarbonate resin fluorescence detection and analysis substrate according to claim 2, wherein the polycarbonate resin obtained by an interfacial polymerization method is in a form of flakes, and the polycarbonate resin fluorescence detection and analysis substrate is produced in a melt molding performed on the flakes.

6. The polycarbonate resin fluorescence detection and analysis substrate according to claim 5, wherein the polycarbonate resin fluorescence detection and analysis substrate is produced using selected flakes containing selected grains having a grain diameter of 500 μm or longer at a content of 90% by weight or higher, the selected grains being obtained in a grain selection of removing micrograins from the flakes.

7. The polycarbonate resin fluorescence detection and analysis substrate according to claim 6, wherein the polycarbonate resin fluorescence detection and analysis substrate is produced using the selected grains obtained from the flakes in the grain selection by use of wind power.

8. The polycarbonate resin fluorescence detection and analysis substrate according to claim 6, wherein the polycarbonate resin fluorescence detection and analysis substrate is produced using the selected grains obtained by removing the micrograins caused to float by use of a ventilation unit.

9. The polycarbonate resin fluorescence detection and analysis substrate according to claim 6, wherein the polycarbonate resin fluorescence detection and analysis substrate is produced using the selected grains obtained from the flakes in the grain selection by use of a sieve.

10. The polycarbonate resin fluorescence detection and analysis substrate according to claim 7, wherein the polycarbonate resin fluorescence detection and analysis substrate is produced using the selected grains obtained from the flakes in the grain selection by use of another sieve.

11. The polycarbonate resin fluorescence detection and analysis substrate according to claim 9, wherein the polycarbonate resin fluorescence detection and analysis substrate is produced using the selected grains obtained by removing the micrograins in a state where the sieve is vibrated.

12. The polycarbonate resin fluorescence detection and analysis substrate according to claim 6, wherein the polycarbonate resin fluorescence detection and analysis substrate is produced using the selected grains having a solution YI value of 1.30 or less.

13. The polycarbonate resin fluorescence detection and analysis substrate according to claim 5, wherein the polycarbonate resin fluorescence detection and analysis substrate is produced using the flakes of the polycarbonate resin having a moisture content of 200 ppm or less as a result of being dried before being subjected to melt molding.

14. The polycarbonate resin fluorescence detection and analysis substrate according to claim 5, wherein the polycarbonate resin fluorescence detection and analysis substrate is produced by melt-molding the selected grains in the melt molding in an atmosphere caused to have an oxygen concentration of 10000 ppm or less by addition of inert gas and/or pressure reduction.

15. The polycarbonate resin fluorescence detection and analysis substrate according to claim 5, wherein the melt molding is an injection molding.

* * * * *